United States Patent
Khormaei et al.

(10) Patent No.: US 10,039,600 B2
(45) Date of Patent: Aug. 7, 2018

(54) APPARATUS AND METHOD FOR SKIN TREATMENT USING PULSED LIGHT

(71) Applicant: L'OREAL, Paris (FR)

(72) Inventors: Iranpour Khormaei, Vancouver, WA (US); Lilac Muller, Woodinville, WA (US); James Christopher McInnes, Seattle, WA (US)

(73) Assignee: L'OREAL, Paris (FR)

( * ) Notice: Subject to any disclaimer, the term of this patent is extended or adjusted under 35 U.S.C. 154(b) by 93 days.

(21) Appl. No.: 14/613,059

(22) Filed: Feb. 3, 2015

(65) Prior Publication Data

US 2016/0220308 A1    Aug. 4, 2016

(51) Int. Cl.
*A61B 18/18* (2006.01)
*A61N 5/06* (2006.01)
*A61B 18/00* (2006.01)
*A61B 17/00* (2006.01)

(52) U.S. Cl.
CPC ............ *A61B 18/18* (2013.01); *A61N 5/0616* (2013.01); *A61B 2017/00172* (2013.01); *A61B 2018/0091* (2013.01); *A61B 2018/00458* (2013.01); *A61B 2018/1807* (2013.01); *A61N 2005/0644* (2013.01); *A61N 2005/0659* (2013.01); *A61N 2005/0662* (2013.01)

(58) Field of Classification Search
CPC .......... A61F 9/008; A61B 18/20; A61B 18/22
USPC ............................................................ 606/3
See application file for complete search history.

(56) References Cited

U.S. PATENT DOCUMENTS

| | | | |
|---|---|---|---|
| 2003/0220556 A1 | 11/2003 | Porat et al. | |
| 2005/0149150 A1 | 7/2005 | McDaniel | |
| 2007/0073276 A1* | 3/2007 | Wilkens | A61N 5/0616 606/9 |
| 2007/0298371 A1* | 12/2007 | Pinyayev | A61C 17/22 433/29 |
| 2009/0024193 A1 | 1/2009 | Altshuler et al. | |
| 2010/0042084 A1* | 2/2010 | Nariyuki | A61B 5/0066 606/15 |
| 2010/0121254 A1 | 5/2010 | McDaniel et al. | |

(Continued)

FOREIGN PATENT DOCUMENTS

DE     19852524 A1 *  5/2000  .......... A61N 5/0616
WO    WO 2011/051941 A1    5/2011

OTHER PUBLICATIONS

English Translation of Abstract of DE 19852524 A1.*

(Continued)

*Primary Examiner* — Daniel Cerioni
(74) *Attorney, Agent, or Firm* — Oblon, McClelland, Maier & Neustadt, L.L.P.

(57) ABSTRACT

An apparatus and method is provided for skin treatment. An apparatus includes an applicator assembly that includes an applicator tip which is configured to apply a normal cyclical mechanical force to a skin surface area of a user and to deliver a skin formulation to a skin surface area of a user. The apparatus further includes an electromagnetic energy assembly that includes at least one electromagnetic energy source adjacent to or within the applicator assembly and is configured to deliver pulses of electromagnetic energy stimulus of a character and for a duration sufficient to penetrate one or more dermal layers within the skin surface area of a use.

12 Claims, 14 Drawing Sheets

(56) References Cited

U.S. PATENT DOCUMENTS

2010/0300480 A1     12/2010   Pilcher et al.
2011/0106067 A1*   5/2011   Geva .................... A45D 34/042
                                                                  606/9
2013/0178916 A1      7/2013   Rylander et al.

OTHER PUBLICATIONS

International Search Report and Written Opinion dated Jun. 30, 2016 in PCT/US2016/016378 filed on Feb. 3, 2016.
U.S. Appl. No. 14/613,125, filed Feb. 3, 2015, Khormaei, et al.

* cited by examiner

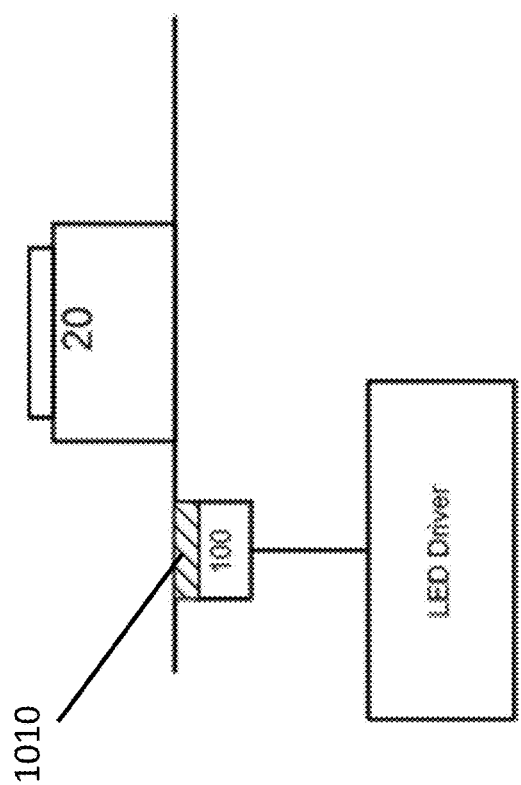

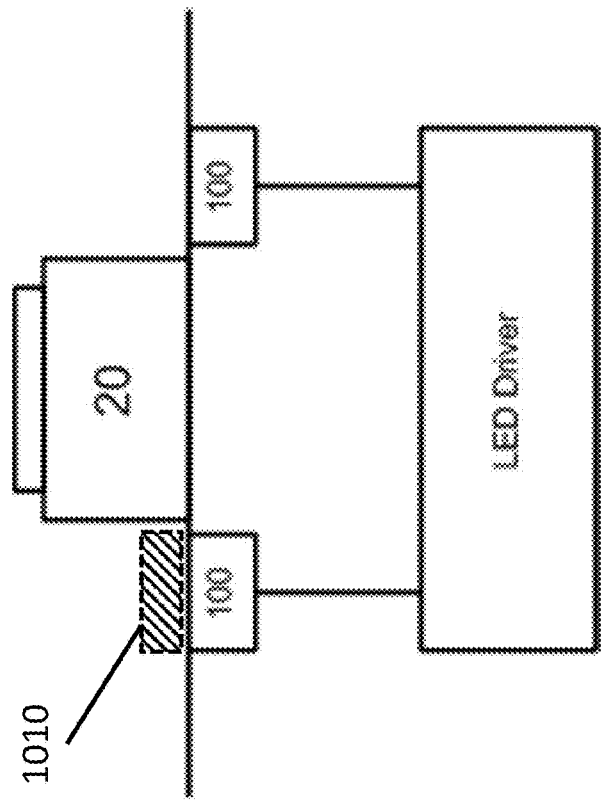
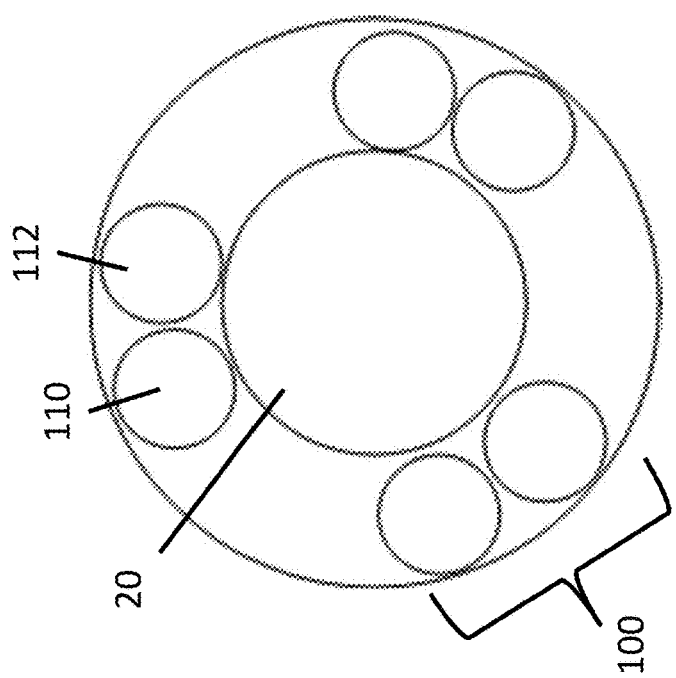
FIG. 12B
FIG. 12A

APPARATUS AND METHOD FOR SKIN TREATMENT USING PULSED LIGHT

BACKGROUND

Field

The disclosure herein generally relates to an apparatus and method for skin treatment which includes applying skin formulations, typically to the skin area, which operate in the sonic frequency range, in combination with electromagnetic radiation to the skin area.

SUMMARY

According to an embodiment, there is provided an apparatus including an applicator assembly that includes an applicator tip which is configured to apply a cyclical mechanical force to a skin surface area of a user and to deliver a skin formulation to a skin surface area of a user. In an embodiment, the cyclical mechanical force includes a normal component. In an embodiment, the cyclical mechanical force includes a shear component. In an embodiment, the cyclical mechanical force includes and normal component and a shear component. In an embodiment, the applicator tip is configured to apply a normal stress and a shear stress to a region of skin.

The apparatus further includes an electromagnetic energy assembly that includes at least one electromagnetic energy source adjacent to or within the applicator assembly and is configured to deliver pulses of electromagnetic energy stimulus of a character and for a duration sufficient to penetrate one or more dermal layers within the skin surface area of a use. In an embodiment, factors that affect penetration depth of electromagnetic energy in tissue include wavelength, frequency, intensity, duration, and the like.

Non limiting examples of electromagnetic energy sources include electromagnetic energy emitters, fiber lasers, laser diodes, lasers, light-emitting diodes, microcavity light-emitting diodes, organic light-emitting diodes, polymer light-emitting diodes, quantum dots, ultra-fast lasers, and the like.

According to an embodiment, the at least one electromagnetic energy source is adjacent to an outer edge of the applicator assembly.

According to an embodiment, the at least one electromagnetic energy source comprises a plurality of light-emitting diodes and is configured to concurrently or sequentially generate at least a first continuous electromagnetic energy stimulus having a peak emissive wavelength of about 590 nanometers and a second continuous electromagnetic energy stimulus having a peak emissive wavelength ranging from about 850 nanometers to about 870 nanometers.

According to an embodiment, the at least one electromagnetic energy source is configured to produce a single dominant emissive wavelength via narrowband multichromatic radiation.

According to an embodiment, the single dominant emissive wavelength is about 590 nanometers.

According to an embodiment, the at least one electromagnetic energy source includes at least one light emitting diode (LED).

According to an embodiment, the at least one light emitting diode (LED) includes a first LED which emits light at a dominant emissive wavelength of about 590 nanometers and a second LED which emits light at about 850-870 nanometers.

According to an embodiment, the first light emitting diode (LED) emits visible yellow light and the second LED emits infrared light.

According to an embodiment, the ratio of power radiation of the first LED to the second LED is 4:1.

According to an embodiment, the first light emitting diode (LED) emits light at about 2 milliwatts per square centimeter ($mW/cm^2$) and the second LED emits light at about 0.5 $mW/cm^2$.

According to an embodiment, an energy fluence of the electromagnetic energy assembly received at the skin surface area is less than about 4 $J/cm^2$.

According to an embodiment, the electromagnetic energy assembly further includes a diffusing lens configured to diffuse light emitted from the electromagnetic energy assembly on the skin to spread an interrogation region.

According to an embodiment, the at least one electromagnetic energy source includes a plurality of electromagnetic energy sources which surround the applicator assembly.

According to an embodiment, the at least one electromagnetic energy source is included within the applicator assembly.

According to an embodiment, the at least one electromagnetic energy source emits pulses of light to the skin surface area of the user at a frequency of about 3 Hz.

According to an embodiment, there is provided a method of skin treatment, implemented by a skin treatment apparatus, including applying a cyclical mechanical force to a skin surface area of a user of a character and for a duration sufficient to cause a compressive force on the skin surface area of a user and to affect the permeability of a skin formulation. The method further includes interrogating the skin surface area of the user with pulses of electromagnetic energy stimulus of a character and for a duration sufficient to penetrate one or more dermal layers within the skin surface area of a user.

According to an embodiment, a method of skin treatment is provided, implemented by a skin treatment apparatus, that includes applying a cyclical mechanical force to a skin surface area of a user of a character and for a duration sufficient to cause a compressive force and a shear force on the skin surface area of a user and to affect the permeability of a skin formulation.

According to an embodiment, the method of skin treatment includes applying the cyclical mechanical force to the skin surface area of a user of a character and for a duration sufficient to cause a compressive force on the skin surface area of a user and to affect the permeability of a skin formulation includes applying a substantially normal oscillating force to the skin surface area.

According to an embodiment, the method includes applying the cyclical mechanical force to the skin surface area of a user of a character and for a duration sufficient to cause a compressive force on the skin surface area of a user and to affect the permeability of a skin formulation includes applying an normal mechanical force having an amplitude of motion perpendicular to the surface of the skin ranging from about 0.01 inches to about 0.075 inches.

According to an embodiment, the method includes interrogating the skin surface area of the user with the pulses of electromagnetic energy stimulus of a character and for a duration sufficient to penetrate at least one or more dermal layers within the skin surface area of a user includes concurrently or sequentially emitting at least a first pulsed electromagnetic energy stimulus having a peak emissive wavelength of about 590 nanometers and a second pulsed electromagnetic energy stimulus having a peak emissive wavelength ranging from about 850 nanometers to about 870 nanometers.

According to an embodiment, the method includes interrogating the skin surface area of the user with the pulses of electromagnetic energy stimulus of a character and for a duration sufficient to penetrate at least one or more dermal layers within the skin surface area of a user includes concurrently or sequentially emitting at least a first continuous electromagnetic interrogation stimulus having a peak irradiance of about 2 milliwatts per square centimeter (mW/cm$^2$) and emitting a second continuous electromagnetic interrogation stimulus having a peak irradiance at about 0.5 mW/cm$^2$.

According to an embodiment, an electromagnetic energy assembly includes at least one electromagnetic energy source adjacent to or within the applicator assembly and configured to deliver a continuous electromagnetic energy stimulus of a character and for a duration sufficient to penetrate one or more dermal layers within the skin surface area of a user and to affect upregulation of one or more epidermis-associated proteins, dermoepidermal-junction-associated proteins, or dermis-associated proteins in the portion of skin.

According to an embodiment, an electromagnetic energy assembly includes at least one electromagnetic energy source adjacent to or within the applicator assembly and configured to deliver a continuous electromagnetic energy stimulus of a character and for a duration sufficient to penetrate one or more dermal layers within the skin surface area of a user and to affect upregulation of one or more epidermal proteins selected from the group consisting of filagrin; transglutaminase 1 (TGK1); glycoprotein (CD44); keratin 10 (K10); keratin 14 (K14); tenacin C; globular actin (ActinG); fibrillar actin (ActinF); and syndecan 1.

According to an embodiment, an electromagnetic energy assembly includes at least one electromagnetic energy source adjacent to or within the applicator assembly and configured to deliver a continuous electromagnetic energy stimulus of a character and for a duration sufficient to penetrate one or more dermal layers within the skin surface area of a user and to affect upregulation of one or more dermoepidermal junction proteins selected from the group consisting of collagen 4 (Coll 4); collagen 7 (Coll 7); laminin V; and perlecan.

According to an embodiment, an electromagnetic energy assembly includes at least one electromagnetic energy source adjacent to or within the applicator assembly and configured to deliver a continuous electromagnetic energy stimulus of a character and for a duration sufficient to penetrate one or more dermal layers within the skin surface area of a user and to affect upregulation of one or more dermal proteins selected from the group consisting of hyaluronan synthase 3 (HAS3); fibronectin; tropoelastin; procoll1; integrin; and decorin.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 10 illustrates an embodiment of the applicator apparatus which includes a diffusing lens.

FIGS. 12A and 12B illustrate an embodiment in which a plurality of light assemblies surround the applicator tip.

Like reference numerals designate identical or corresponding parts throughout the several views.

DETAILED DESCRIPTION

Power appliances for applying skin formulations, typically to the skin area, which operate in the sonic frequency range, are effective for producing significant absorption of the skin formulation to improve skin appearance, and are also comfortable with respect to the physical contact between the applicator and the skin. Such an appliance, is described in U.S. Pat. No. 8,469,909, which is owned by the assignee of the present application, and the contents of which are incorporated by reference.

Light therapy can be used for treatment of skin conditions using narrowband light. Many such light therapy devices illuminate are very large and are used to illuminate the entire face in a stationary manner.

However, there is currently no device which effectively combines the benefits of a sonic application of a skin formulation with the benefits of light therapy into a single compact personal appliance that is convenient, inexpensive, and simple to use.

Figure 1:
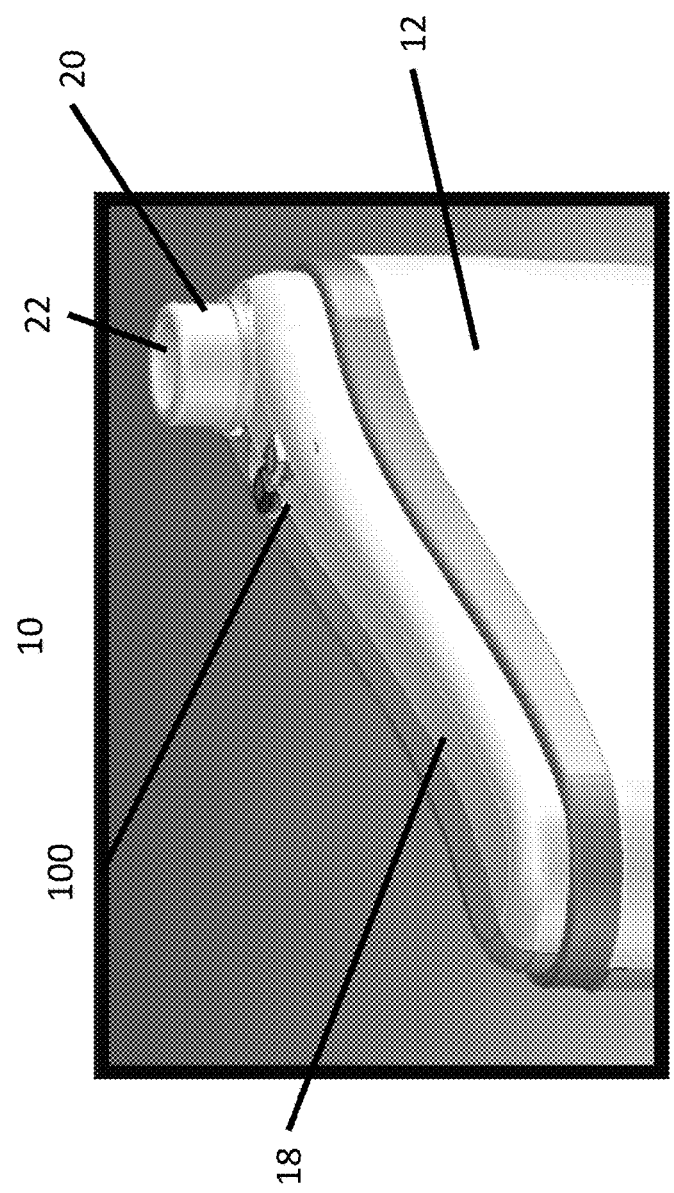
FIG. 1 illustrates an applicator apparatus according to an embodiment.

FIG. 1 shows an applicator appliance, in which one or more methodologies or technologies can be implemented such as, for example, concurrently or sequentially providing a normal cyclical mechanical force and a plurality of electromagnetic stimuli to a facial area of a user. In an embodiment, an applicator appliance includes a body portion 12, which is separate from a cap portion (not shown). Extending from the upper surface 18 of body portion 12 is an applicator tip 20 which contacts the skin of the user. In an embodiment, the applicator tip 20 comprises one or more elastomeric materials. In an embodiment, the applicator tip 20 comprises one or more polymeric materials. In an embodiment, the applicator tip 20 is formed from silicone. In an embodiment, the applicator tip 20 is formed from super soft silicone having a shore 00-30 hardness. Further non-limiting examples of applicator tip materials include ethylene propylene diene rubbers, flourosilicones, chemical resistant materials, and the like.

In an embodiment, the applicator tip 20 comprises one or more waveguides operably coupled to at least one electromagnetic energy emitter. In an embodiment, the applicator tip 20 comprises one or more transparent, translucent, or light-transmitting materials.

Among transparent, translucent, or light-transmitting materials, examples include those materials that offer a low optical attenuation rate to the transmission or propagation of light waves. In an embodiment, the applicator tip 20 comprises one or more optically clear materials, semi-clear materials, plastics, thermo plastics, polymers, resins, thermal resins, and the like. In an embodiment, the applicator tip 20 comprises one or more of acetal copolymers, acrylic, glass, AgBr, AgCl, $Al_2O_3$, GeAsSe glass, $BaF_2$, $CaF_2$, CdTe, AsSeTe glass, CsI, diamond, GaAs, Ge, ITRAN materials, KBr, thallium bromide-Iodide, LiF, $MgF_2$, NaCl, polyethylene, Pyrex, Si, $SiO_2$, ZnS, ZnSe, thermoplastic polymers, thermoset polymers, and the like.

Further non-limiting examples of optically transparent, translucent, or light-transmitting materials include one or more of acrylonitrile butadaine styrene polymers, cellulosic, epoxy, ethylene butyl acrylate, ethylene tetrafluoroethylene, ethylene vinyl alcohol, fluorinated ethylene propylene, furan, nylon, phenolic, poly[2,2,4-trifluoro-5-trifluoromethoxy-1,3-dioxole-co-tetrafluoroethylen-e], poly[2,2-bistrifluoromethyl-4,5-difluoro-1,3-dioxole-co-tetrafluoroeth-ylene], poly[2,3-(perfluoroalkenyl) perfluorotetrahydrofuran], polyacrylonitrile butadiene styrene, polybenzimidazole, polycarbonate, polyester, polyetheretherketone, polyetherimide, polyethersulfone, polyethylene, polyimide, polymethyl methacrylate, polynorbornene, polyperfluoroalkoxyethylene, polystyrene, polysulfone, polyurethane, polyvinyl chloride, polyvinylidene fluoride, diallyl phthalate, thermoplastic elastomer, transparent polymers, vinyl esters, and the like.

In an embodiment, the applicator tip 20 is configured to deliver a continuous electromagnetic energy stimulus of a character and for a duration sufficient to penetrate one or more dermal layers within the skin surface area of a user. For example, in an embodiment, the applicator tip 20 comprises an optically transparent, translucent, or light-transmitting materials; is operably coupled to one or more electromagnetic energy emitters; and is configured to generate a continuous electromagnetic energy stimulus of a character and for a duration sufficient to penetrate one or more dermal layers within the skin surface area of a user. In an embodiment, factors that affect penetration depth of electromagnetic energy in tissue include wavelength, frequency, intensity, and the like.

In the embodiment shown, applicator tip 20 includes a concave portion 22 at a forward end thereof. The concave portion will temporarily hold a selected quantity of a skin formulation which is to be applied to the user's facial skin area during operation of the appliance. Included in the upper surface 18 is an LED light assembly 100, the installation of which will be described in more detail later in this document. The appliance is controlled by an on/off switch (not shown).

For effective operation of the appliance, specifically, operation which produces effective absorption of the skin formulation, with a comfortable contact between the applicator tip and the user's skin, a complex motion of the applicator tip 20 has been found to be important. A first component of the applicator tip motion is perpendicular to the surface of the skin, a second component of motion is parallel to the surface of the skin, and a third component is arcuate which results in progressively increasing contact between the applicator tip and the skin.

Figure 2:
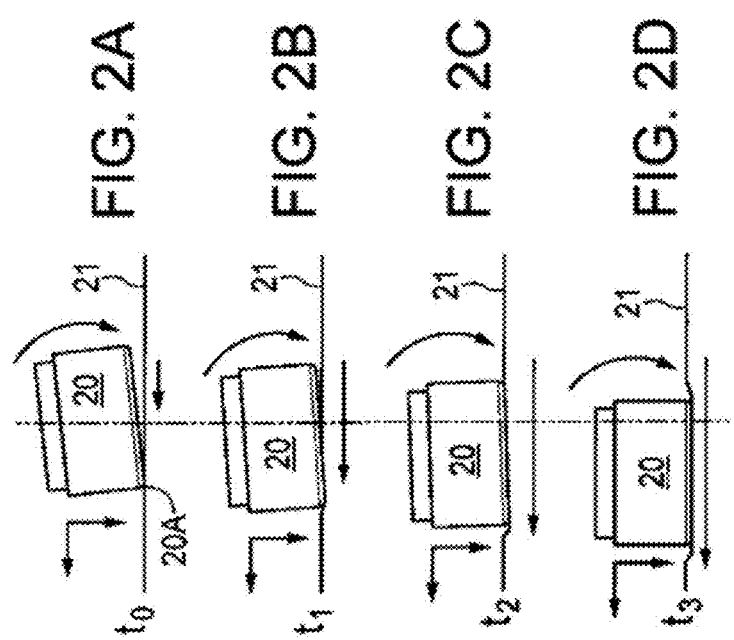
FIGS. 2A, 2B, 2C, and 2D illustrate a sequence of a desired motion of an applicator tip of the applicator apparatus.

FIG. 2 shows a sequence of this desired motion. At a time t0 (FIG. 2A), initial contact between applicator tip 20 and skin area 21 is shown. The inside edge 20A of the applicator tip 20 comes first into contact with the surface of the skin 21. Force is beginning to be applied downwardly, perpendicular to the surface of the skin, producing an initial amount of compressive force on the skin. Initial tensile stress is also produced on the skin 21. At time t1 (FIG. 2B), applicator tip 20 is rotating clockwise as well as moving downwardly perpendicular to and against the skin, continuing to compress the skin, as shown. In addition, the applicator tip moves to the left, parallel to the surface of the skin 21. This parallel motion component produces a sufficient but relatively small tensile stress in the skin, which when combined with the compressive force has been discovered to be important in improving absorption of skin formulations but without damaging the skin or causing discomfort.

The applicator tip motion changes at time t2 (FIG. 2C), and again at time t3 (FIG. 2D), at which point the contacting surface of the applicator tip is essentially parallel to the surface of the skin 21 with the contacting surface of the applicator tip in full contact with the skin, and with both the compressive force perpendicular to the skin and the tensile stress parallel to the surface of the skin reaching a maximum value. The applicator tip produces a compressive force against the skin along the entire contacting surface of the applicator tip, as shown in FIG. 2D. The motion of the applicator tip then is reversed by motor action, with the applicator tip ending up at its initial position. The sequence 2A-2D is then repeated, at a selected frequency.

It has been discovered that the progressively increasing contact between the surface of the skin due to the arcuate component of the applicator tip motion is important in maintaining a comfortable contact, i.e. sensation, in the user. The above described motion, while complex, has the dual advantage of producing effective absorption of the skin formulation as well as maintaining a satisfactory comfortable level of contact for the user, such that the average user will continue to use the applicator. The complex motion, combined with the concave shape of the forward surface of the applicator tip, helps to keep the quantity of skin formulation present in the concave portion from being immediately displaced from the area of application on the user's skin.

Figure 3:
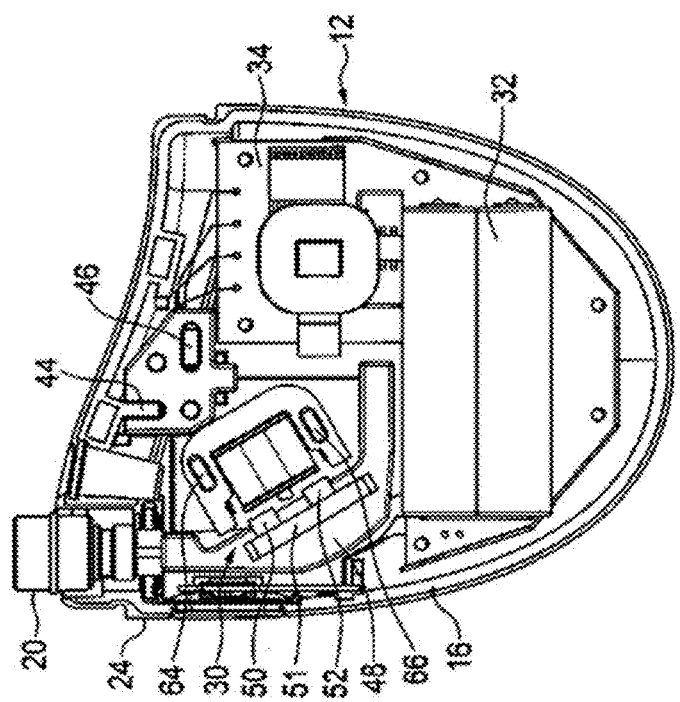
FIG. 3 is a cross-sectional diagram showing the overall operating parts contained within the applicator apparatus.

FIG. 3 is a cross-sectional diagram showing the overall operating parts contained within the appliance body 12. The appliance body 12 includes a motor referred to generally at 30, which will be described in more detail below, and a source of power, which in the embodiment shown are rechargeable batteries 32, but which could be other power sources as well, such as primary cells or an external power supply. The control signal to the motor, as well as other operational control functions, such as sensing the state of the on/off switch 24, controlling the duration of a single application use and monitoring battery charge state are provided by a microprocessor 34. Microprocessor 34 is conventional in structure and operation for such an appliance. All of the above parts are contained within housing portion 16 of body 12 of the appliance.

Figure 4:
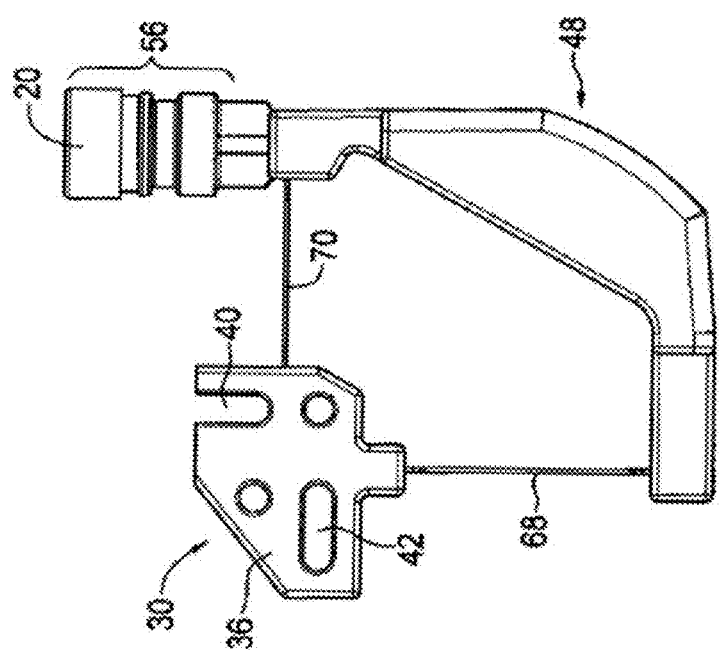
FIG. 4 illustrates a first view of the motor and its related components of the applicator apparatus.
Figure 5:
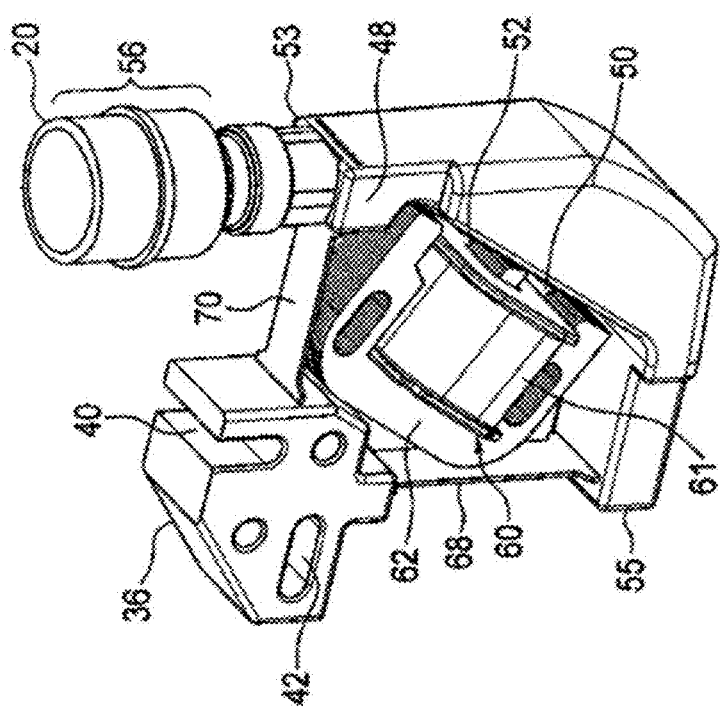
FIG. 5 illustrates a second view of the motor and its related components of the applicator apparatus.
Figure 6:
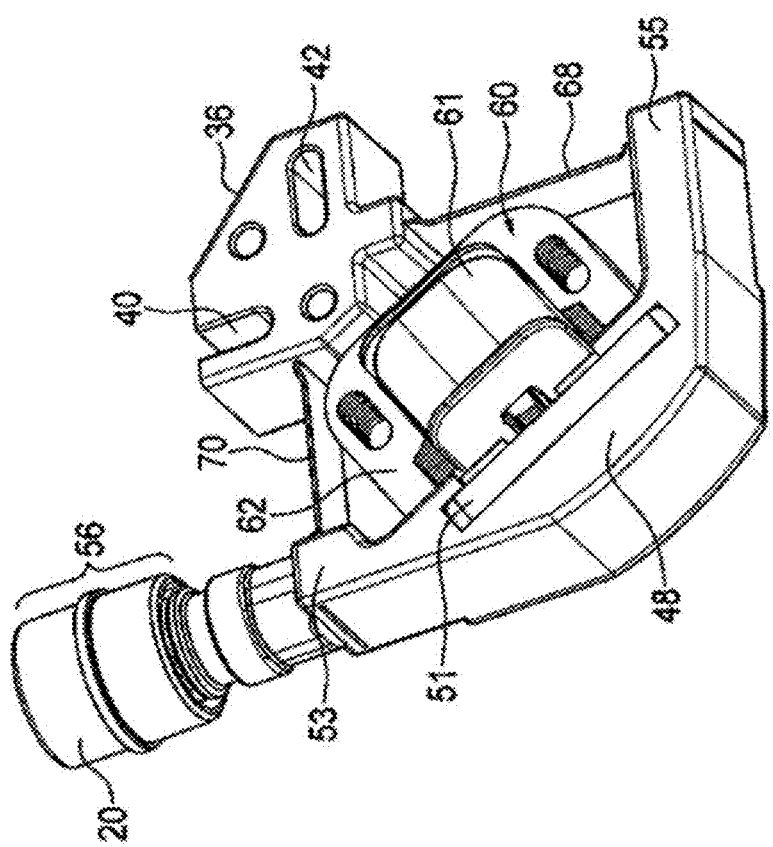
FIG. 6 illustrates a third view of the motor and its related components of the applicator apparatus.
Figure 7B:
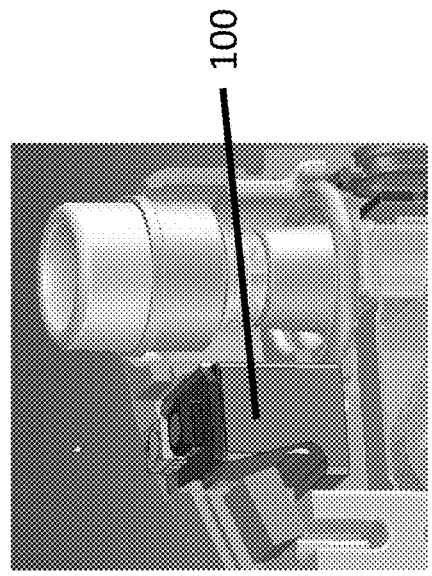
FIGS. 7A, 7B, 7C, and 7D illustrate a method of installing a lighting unit into a housing of the applicator apparatus.
Figure 7D:
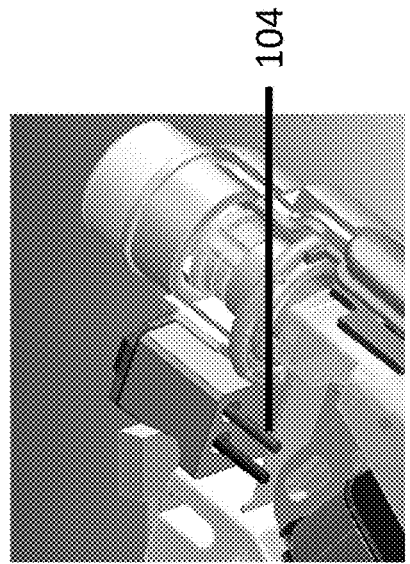
Figure 7A:
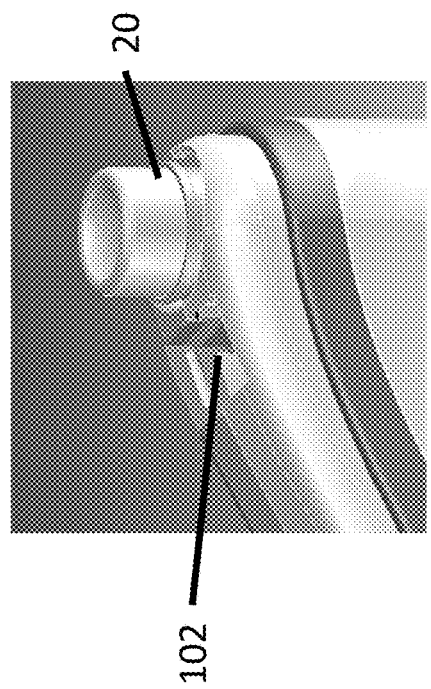
Figure 7C:
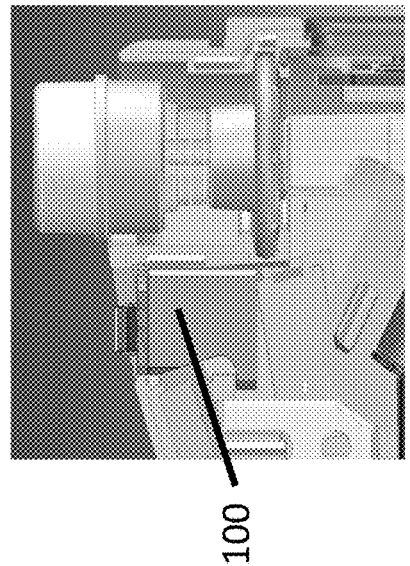

FIGS. 4-6 show the motor 30 for the appliance in more detail. The motor includes an anchor member 36 which is made from a stiff material which, in the embodiment shown, is hard plastic. The anchor member in the embodiment shown includes two slots 40 and 42 which are at right angles to each other, and which fit securely into corresponding rib elements 44 and 46 which are part of the housing portion 16 (FIG. 3). The anchor member 36 is thus fixed in position in the housing and is not free to move during operation of the motor.

Motor 30 also includes an armature assembly 48 which includes two spaced permanent magnets 50 and 52 mounted on a metal backiron 51 (FIGS. 3, 6). In the embodiment shown, the permanent magnets are spaced approximately 0.18 inches apart, but this can be varied. Further, the permanent magnets, in the embodiment shown, are 0.15 inches square by 0.1 inches thick, although these dimensions can also vary.

At one end 53 of the armature member 48 is a removable applicator tip assembly 56, at the forward end of which is positioned applicator tip 20. The applicator tip 20 is described in more detail in co-pending U.S. patent application Ser. No. 12/474,426, owned by the assignee of the present disclosure, the contents of which are hereby incorporated by reference. The applicator tip has a concave forward surface, to hold the skin formulation and is made from a very soft material, Shore scale OO Durometer 30. The flexibility of the material is similar to that of human skin and thus transmits motion and force efficiently.

Positioned between anchor member 36 and armature 48 is an electromagnetic stator assembly 60. The electromagnetic stator assembly 60 includes a conventional electromagnet 61 and an E-core laminated stack 62, the outer legs of which are separated from the center leg by 0.257 inches and 0.267 inches, respectively, in the embodiment shown. The stator poles are the ends of the three legs. The stator assembly is mounted to two opposing ribs 64 and 66 which are also part of housing portion 16. Hence, in operation of the motor the stator assembly 60 also remains fixed in position.

The motor further includes two leaf springs 68 and 70 which extend between and connect anchor member 36 and opposing extending end portions 53 and 55 of armature 48.

The extending end portions of armature 48 are at right angles to each other. In the embodiment shown, the leaf springs are approximately 0.2 inches wide and 0.012 inches thick and are made of stainless steel. The leaf springs 68 and 70 also extend approximately at right angles to each other. Leaf springs 68 and 70 have different free lengths. The ratio of the free lengths of the leaf springs is important to achieve the desired multi-component motion of the applicator tip to produce effective and comfortable application of skin formulations. The ratio of the length of spring 70 to the length of spring 68 is within the range of 0.75:1 to 0.95:1. In an embodiment, the free length ratio is within the range of 0.79:1 to 0.83:1. When the appliance is properly oriented relative to the skin, leaf spring 68 will be approximately perpendicular to the skin, while leaf spring 70 will be approximately parallel with the skin. It is this arrangement of leaf springs which produces the desired combination of effective absorption of skin formulation and comfort to the user.

In operation, following actuation of the on/off switch 24, an alternating current electrical signal from microprocessor 34 is provided to the electromagnetic stator assembly 60. During one half cycle of the alternating current signal, the two outer poles of the electromagnet will attract one of the permanent magnets and repel the other permanent magnet. The center pole will also repel one permanent magnet while attracting the other. The resulting force moves armature 48, including the applicator tip, in a complex slightly arcuate motion counterclockwise (as viewed in FIG. 5) relative to the stator assembly 60 and toward the skin. This motion, as indicated above, and as shown in FIG. 2A-2D, includes a component of perpendicular motion, a component of parallel motion and a small component of arcuate motion. On the other half cycle, the direction of the current is reversed, and the armature responds by moving the tip applicator away from the skin in a clockwise direction relative to the stator.

The frequency of the action is typically within a range of 50-200 Hz. In an embodiment, the frequency of the action ranges from about of 110 Hz to about 135 Hz. The range of amplitude of the motion perpendicular to the surface of the skin is within the range of 0.01 inches to 0.075 inches. In an embodiment, the range of amplitude of the motion perpendicular to the surface of the skin ranges from about 0.02 inches to about 0.035 inches. The range of motion parallel to the surface of the skin is within the range of 0.005 inches to 0.07 inches. In an embodiment, the range of motion parallel to the surface of the skin ranges from about 0.013 inches to about 0.032 inches. The arcuate motion that results from these dimensions is relatively small, following an arc in the range of 0.5°-3°. In an embodiment, the arcuate motion that results from these dimensions is about 2°, although this value will vary with the actual dimensions used.

In operation, leaf springs 68 and 70 act to both center the armature when it is at rest and to produce a mechanically resonant system when combined with the mass of the moving armature and the applicator tip assembly. When the electrical current alternates direction at a frequency roughly equal to the mechanical resonance of the overall system, the amplitude of motion of the armature structure increases significantly, thus producing the required motion for effective action with the desired high efficiency relative to the electrical power input. Hence, the appliance is both effective in producing rapid and effective absorption of the skin formulation, but also is a practical appliance to operate.

In one embodiment, the above-described structure further includes single or multiple light sources, to produce either a single dominant emissive wavelength, i.e., a narrowband multichromatic radiation, or multiple wavelengths (either monochromatic, narrowband multichromatic, wideband multichromatic, or combinations thereof). The single or multiple combinations may be applied either simultaneously or sequentially.

Although preferred embodiments of the present disclosure may use LEDs, ultrasound and/or laser or light energy, the present disclosure is not limited to the use of these energy sources. Other sources of energy, including (without limitation) microwave energy and radio frequency energy may also be used. Exemplary of known light sources are fluorescent lights, flashlamps, filamentous lights, etc. One skilled in the art will recognize that any light source capable of emitting electromagnetic radiation at a medically useful wavelength, as described herein, directly, or by means of optical filtration, is within the scope of suitable light sources according to the present disclosure. For purposes of the photomodulatory and photothermal treatment methods described, any source capable of emitting light having a wavelength from about 300 nm to about 1400 nm, or producing electromagnetic radiation which is filtered or otherwise altered to exposure the skin, a topical composition, or other component of the present treatment regime to a wavelength of light in the aforementioned range is medically useful.

The targeted skin may be exposed to one or more wavelengths of LED, laser or non-laser light such as filtered filamentous sources or fluorescent sources or single or multiple frequencies of ultrasound. A variety of parameters may be used (including pulse duration, energy, single or multiple pulses, the interval between pulses, the total number of pulses, etc.) to deliver sufficient cumulative energy to interact with the agent or tissue complex. This results in the inhibition or destruction of the sebaceous oil gland or the supporting skin tissue through photomodulatory means, photothermal means, or combinations thereof. In an embodiment, these devices may be used by the patient for at-home treatment or as part of an ongoing skin-care system after receiving treatment by a physician.

Wavelength—Each target cell or subcellular component, or molecular bond therein, tends to have at least one unique and characteristic "action spectrum" at which it exhibits certain electromagnetic or light absorption peaks or maxima. Different cell lines (of the same cell—for example fibroblasts from 3 different patients) exhibit some differences in their absorption spectra and thus using narrow band multichromatic light (rather than monochromatic light) is also useful in producing the optimal clinical effect. When these cells or subcellular components are irradiated with wavelengths corresponding to the absorption peaks or maxima, energy is transferred from the light photon and absorbed by the target. The particular features of the delivered energy determine the cellular effects. The complexity of these combinations of parameters has produced much confusion in the prior art. Basically, the wavelength should roughly correlate with an absorption maxima for the target cell or subcellular component or tissue, or exogenous chromophore. In some cases it may be desirable to target more than one maxima—either simultaneously or sequentially on the same or different treatment dates. The presence of multiple maxima action spectra are common for a given cell or subcellular component or exogenous chromophore and different wavelength maxima irradiation may produce different results.

If the wavelength band is overly broad, then the desired photomodulation effects may be altered from those intended. Consequently, use of broad band noncoherent intense light sources may be less desirable than those specified for use with the present disclosure, in contrast to the use of multiple narrowband emitters. The laser diodes are also multichromatic with narrow wavelength bands around a dominant band, i.e., they are narrowband multichromatic devices—devices which emit electromagnetic in a narrow band of radiation either symetrically or asymetrically around a dominant wavelength. In an embodiment, a narrowband multichromatic electromagnetic radiation emitter emits electromagnetic radiation in a bandwidth of +/−about 100 nanometers around a dominant wavelength. In an embodiment, a narrowband multichromatic electromagnetic radiation emitter emits electromagnetic radiation in a bandwidth of +/−about 50 nanometers around a dominant wavelength. In an embodiment, a narrowband multichromatic electromagnetic radiation emitter emits electromagnetic radiation in a bandwidth of +/−about 20 nanometers around a dominant wavelength. In an embodiment, a narrowband multichromatic electromagnetic radiation emitter emits electromagnetic radiation in a bandwidth of +/−about 10 nanometers around a dominant wavelength. In an embodiment, a narrowband multichromatic electromagnetic radiation emitter emits electromagnetic radiation in a bandwidth of +/−about 6.5 nanometers around a dominant wavelength. LEDS, while not monochromatic, emit in such a narrow band as to be considered narrowband multichromatic emitters. The narrow band allows photons of slightly different wavelengths to be emitted. This can potentially be beneficial for creating certain desirable multi photon interactions. In contrast, most commercial lasers emit light at a single wavelength of light and are considered monochromatic. The use of lasers, according to the prior art, has relied upon the coherent, i.e., monochromatic, nature of their electromagnetic emissions.

Wavelength may also determine tissue penetration depth. It is important for the desired wavelength to reach the target cell, tissue or organ. Tissue penetration depth for intact skin may be different than the tissue penetration depth for ulcerated or burned skin and may also be different for skin that has been abraded or enzymatically peeled or that has had at least a portion of the stratum corneum removed by any method. It is also important to penetrate any interfering chromophore that also absorbs at this same wavelength (e.g. dark ethnic skin, plastic Petrie dishes for tissue or cell culture, etc.). It is important to penetrate any tissues or organs in its pathway.

For example, light having a dominant wavelength emission in the range of about 400 nm to about 420 nm has such a short wavelength that not all sebaceous glands or acne cysts can be effectively treated due to the limited depth of penetration of the radiation, whereas light having a wavelength of about 600 nm to about 660 nm can more easily penetrate to a greater depth, if treatment of the lower dermal layers or even deeper is desirable. Accordingly, the selection of the dominant wavelength of the radiation emitter is also dependent on the depth of treatment desired. The selection of the proper wavelength is one of the significant parameters for effective use of the present disclosure, but others are important as well:

Energy Density—The energy density corresponds to the amount of energy delivered during irradiation and is also referred to as energy intensity and light intensity. The optimal 'dose' is affected by pulse duration and wavelength—thus, these are interrelated and pulse duration is very important—in general high energy produces inhibition and lower energy produces stimulation.

Pulse duration—The exposure time for the irradiation is very critical and varies with the desired effect and the target cell, subcellular component, exogenous chromophore tissue or organ (e.g. 0.5 microseconds to 10 min may be effective for human fibroblasts, though greater or lesser may also be used successfully).

Continuous Wave (CW) vs. pulsed—e.g. the optimal pulse duration is affected by these parameters. In general, the energy requirements are different if pulsed mode is used compared to continuous (CW) modes. Generally, the pulsed mode is preferred for certain treatment regimen and the CW mode for others.

Frequency (if pulsed)—e.g. higher frequency tends to be inhibitory while lower frequency tends to be stimulatory, but exceptions may occur.

Duty cycle—This is the device light output repetition cycle whereby the irradiation is repeated at periodic intervals, also referred to herein as the interpulse delay (time between pulses when the treatment session comprises a series of pulses).

Suitable active agents for use in topical compositions applied to the skin by the applicator tip 20 in accordance with the present description include one or more of Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, bacteriochlorophyll, copper chlorophyllin, chloroplasts, carotenoids, phycobilin, rhodopsin, anthocyanin, and derivatives, subcomponents, immunological complexes and antibodies directed towards any component of the target skin structure or apparatus, and analogs of the above items both natural and synthetic, as well as combinations thereof.

Further non-limiting examples of topical compositions applied to the skin by the applicator tip include anti-wrinkle compositions (e.g., PRO-XYLANE™, and the like), anti-dark circle compositions (e.g., HALOXYL™, and the like), or anti-puffiness compositions (e.g., FRIMALIFT™, and the like).

Further non-limiting examples of active agents for use in topical compositions applied to the skin by the applicator tip include xyloses, hydroxypropyl tetrahydropyrantriol and the like.

Further non-limiting examples of active agents for use in topical compositions applied to the skin by the applicator tip include capryloyl salicylic acid, adenosine, adenosine triphosphate, retinol linoleate, and the like.

In an embodiment, an applicator assembly includes an applicator tip that is configured to apply a cyclical mechanical force to a skin surface area of a user and to deliver a skin formulation including one or more of Acrylates/C10-30 Alkyl Acrylate CrossPolymer, Adenosine, Alcohol, Arginine, BHT, BIS-PEG-18 Methyl Ether Dimethyl Silane, Butylene Glycol, Caffeine, Capryloyl Salicylic Acid, Caprylyl Glycol, Carbomer, centaurea cyanus flower water, chlorhexidine digluconate, chrysin, Citric Acid, Coco-Betadine, Cyclohexasiloxane, dimethicone, Disodium Ethylenediaminetetraacetic acid (EDTA), Glycerin, Hydrogenated Lecithin, Hydroxypropyl Tetrahydropyrantriol, Lauroyl Lysine, Methyl Gluceth-20, N-Hydroxysuccinimide, Octyldodecanol, Palmitoyl Oligopeptide, Palmitoyl Tetrapeptide-7, Polyethylene Glycol (PEG)-20, Pentylene Glycol, Phenoxyethanol, Polysilicone-11, Potassium Sorbate, Propanediol, Propylene Glycol, Sodium Hydroxide, Squalane, Steareth-20, Tocopheryl acetate, Water, Xanthan Gum, Yeast Extract, and the like.

In an example, a device emits narrowband, multichromatic electromagnetic radiation with a dominant emissive wavelength of about 590 nm (+/−about 10 nm) and also some light in the 850-870 nm range and, optionally, a small amount in the 1060 nm range. It has been discovered that the combination of the visible 590 and the infrared 850-870 nm is bioactive. A special IR filter may also be added to reduce the IR component of the radiation that the target skin or tissue is exposed to, as this is believed to unsymmetrically dampen the shape of the IR/850 curve. At 850-870 nm, there is believed to be a 'dose dependent' effect on fibroblasts. Further, at a power level of about 1 mW/cm$^2$, photomodulation occurs for anti aging phenotype effect (those skilled in the art will recognize that power meters cannot measure this precisely, so there may be some variation/error in meter methods). Generally, where a treatment that does not cause thermal injury is desired, an energy fluence of less than about 4 J/cm$^2$ (+/−0.5 J/cm$^2$) is preferable.

The ratio of yellow light to IR radiation in the radiation used for treatment has been found to have an effect on the overall performance of the present system. Specifically, through testing with monochrometer and single wavelength LEDs, and later using ratio DNA microarrays studies it was determined that one specific combination ratio of yellow and IR was very effective for wrinkles. Relative amounts of each type of radiation are believed to be important, more so than the actual radiation level (provided that ablation does not occur). At about 2.0 mW/cm$^2$ (+/−about 0.5 mW/cm$^2$) for 590 nm and about 0.5 mW/cm$^2$ (+/−about 0.5 mW/cm$^2$) for the 850-870 nm (i.e., a 4:1 ratio of yellow to IR) has been found to produce good results. Another factor to consider is the shape of the amplitude vs. wavelength curve for the IR component of the system.

FIG. 7 shows a method of installing the lighting unit into the housing 12. As shown in FIG. 7A, a slot or hole is created proximal to the applicator tip 20. As shown in FIGS. 7B and 7C, LED assembly 100 is inserted into the slot. As shown in FIG. 7D, the wiring 104 for the LED assembly 100 is routed to a driver circuit and a power supply as will be explained below.

Figure 8:
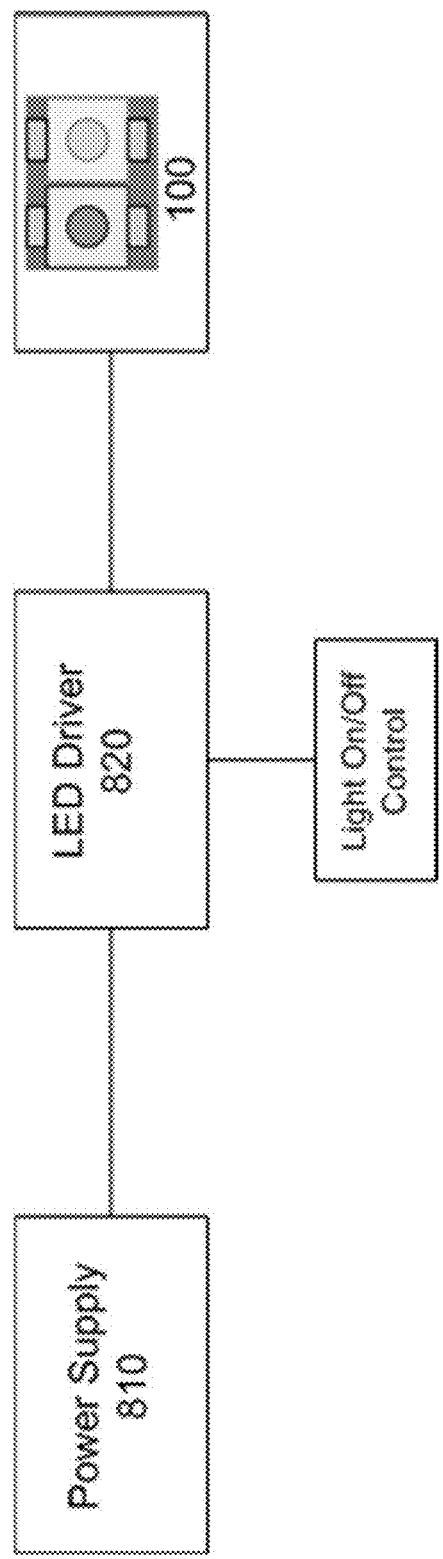
FIG. 8 shows a block diagram of hardware components used in conjunction with the LED assembly.

FIG. 8 shows a block diagram of hardware components used in conjunction with the LED assembly 100. The LEDs in LED assembly are driven by an LED Driver Board 820, which in turn receives power from Power Supply 810. Power Supply can be the same or different from batteries 32 mentioned above. Additionally, LED Driver 820 can be included as part of microprocessor 34 mentioned above, or it can be an independent component. FIG. 8 also shows that the LED Driver 820 can be connected to a light on/off control unit which receives an input from the user to toggle on/off the LED units.

Figure 9B:
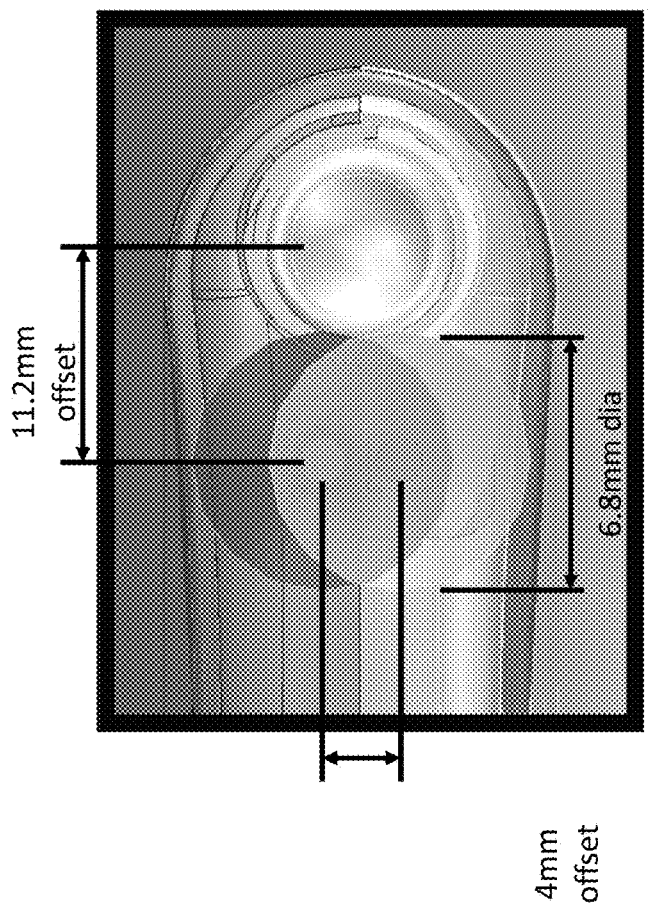
FIGS. 9A and 9B illustrate details of the individual lighting units contained in the LED assembly.
Figure 9A:
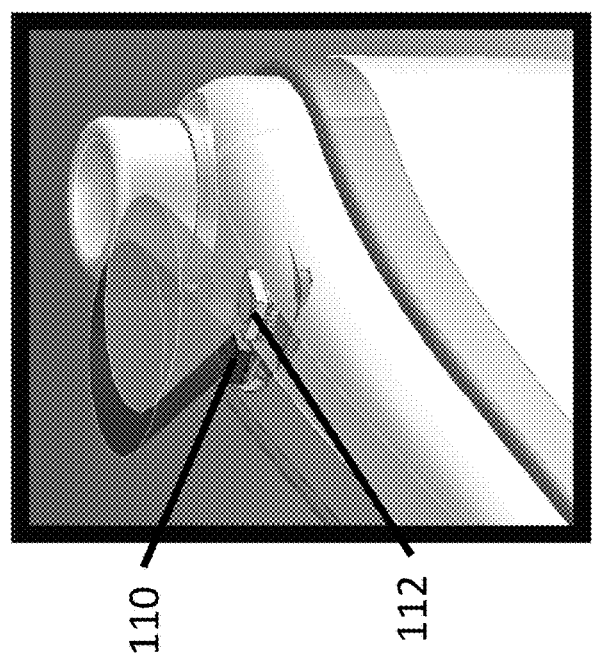

FIG. 9A shows that the LED assembly includes an infrared LED unit 110 and a yellow LED unit 112, which each emit a cone-shaped beam of light. The LED units can be standard commercially available LEDs as known to a person of ordinary skill in the art. For instance, the LEDs could be types LY G6SP-CADB-36-1-Z (for providing the 590 nm wavelength) and VSMF4720 (for providing the 870 nm wavelength).

FIG. 9B shows that the LEDs 110 and 112 are spaced apart by 4 mm, and the LEDs are spaced apart from the applicator tip by 11.2 mm. When the LEDS are configured to emit light at an 80 degree cone angle, this produces light intensity at 77% with no tip occlusion from the applicator tip.

FIG. 10 shows an embodiment which further includes a lens 1010 used in conjunction with the LED units to diffuse or broaden the light exposure of a specific area. The lens 1010 can have positive or negative focal length properties to achieve the desired emission of light, and can be made of any number of materials, such as, but not limited to, glass, plastic, or resin. In one example, an acrylic material placed external to the LED units may be used to achieve such a diffusing lens.

In conventional light therapy systems, a pulse scheme is used for the light emissions on the skin surface. A 'code' refers to the pulse scheme for various treatment regiment. This includes various factors such as pulse length, interpulse delay, and pulse repetition. For example a treatment may comprise a pulse code of 250 msec "on" time, 100 msec "off" time (or dark period), and 100 pulses. This produces a total energy fluence, in J/cm$^2$, of 25 seconds times the power output level of the emitters. This permits a comparison of pulsed versus continuous wave treatment (the "code" for continuous wave treatment would be 1 pulse, an "on" time of whatever the treatment length is chosen to be, and an "off" time of 0 sec.)

Figure 11:
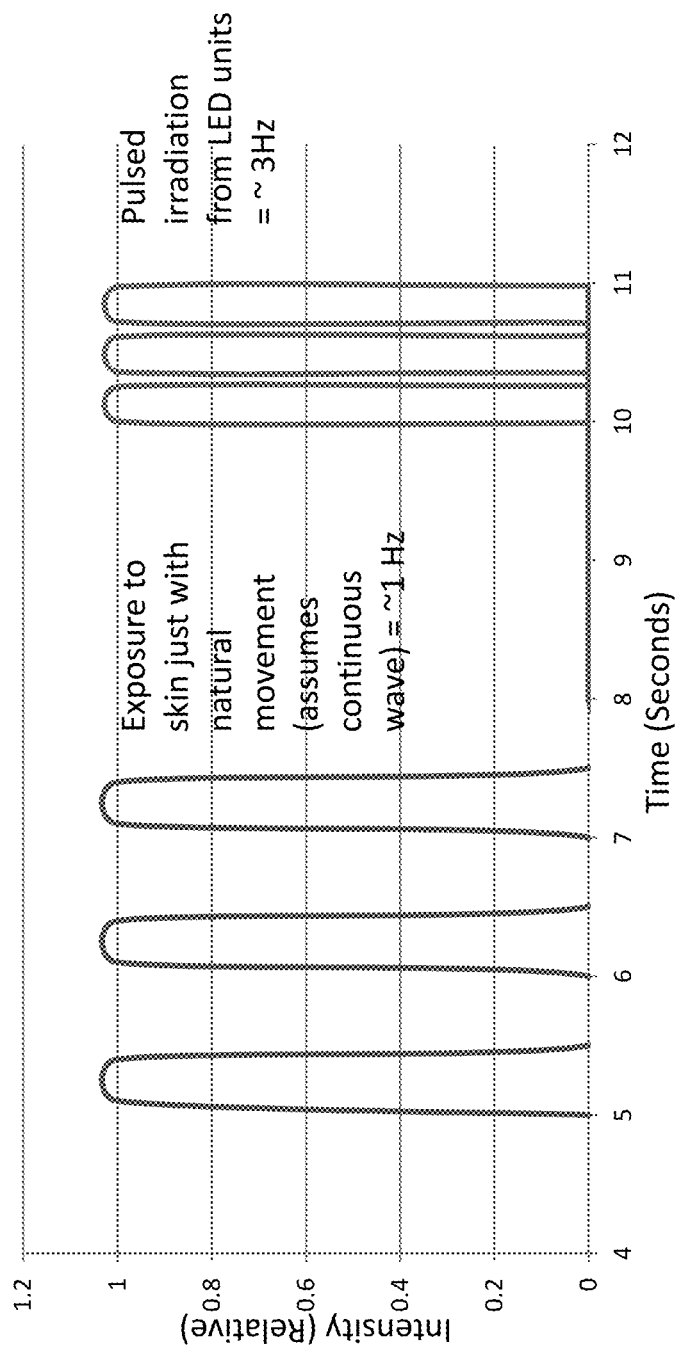
FIG. 11 illustrates a frequency of pulsing of the received light at the surface of the skin of a user.

The present embodiment allows for use of pulsed wave treatment of 3 Hz pulsed waves on the skin surface of the user as shown in the right side of FIG. 11. This is accomplished by assuming no movement of the device over an isolated skin area since natural movement alone may produce the effect of 1 Hz pulses as shown on the left side of FIG. 11. However, the claimed disclosure is not limited to 3 Hz pulsed treatment and may be more or less as needed.

In a modification to the embodiment described above, one or a plurality of LED assemblies 100 (which may include LED units 110 and 112) are provided such that they surround the applicator tip 20, as shown in FIGS. 12A and 12B. The lens 1010 described above may optionally be provided with each LED assembly 100 to focus or diffuse the emitted light.

Figure 13B:
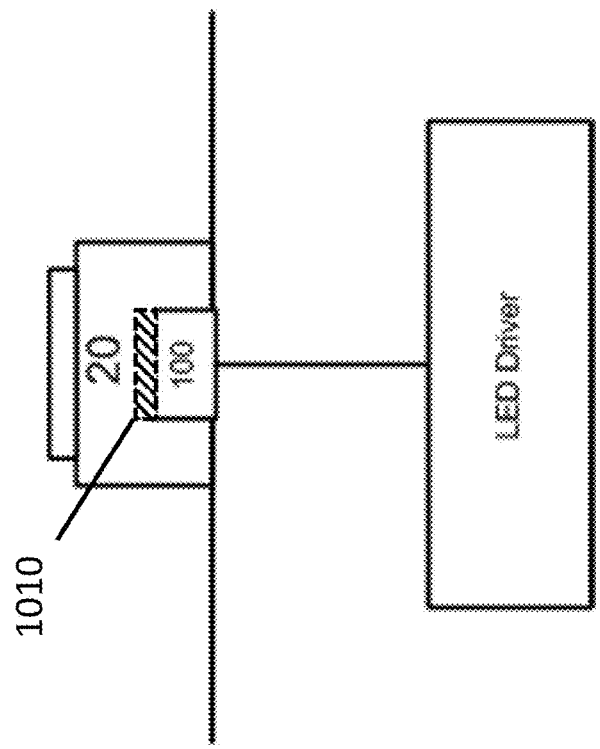
FIGS. 13A and 13B illustrate an embodiment in which a light assembly is included within the applicator tip.
Figure 13A:
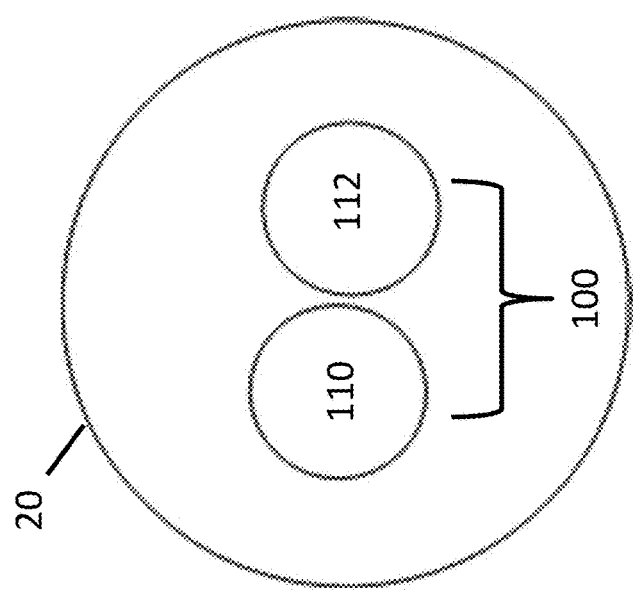

In another modification, the LED assembly 100 may be provided within the applicator tip itself as shown in FIGS. 13A and 13B. The lens 1010 described above may optionally be provided with the LED assembly 100 to focus or diffuse the emitted light.

Figure 14:
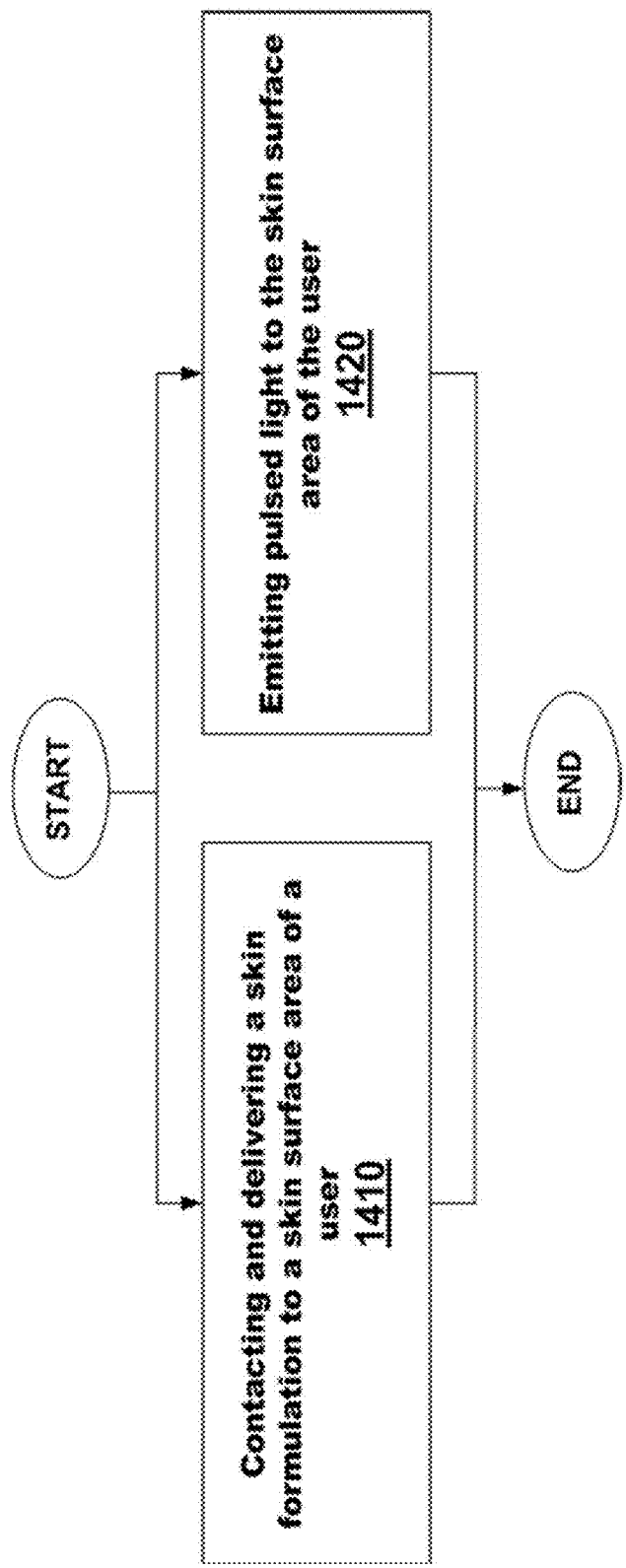
FIG. 14 illustrates an embodiment of a process performed by the applicator apparatus.

FIG. 14 shows a method implemented by the applicator apparatus 10 described above. In step 1410, the applicator tip assembly 20 performs a process of contacting and delivering a skin formulation to a skin surface of a user according to the cyclic movement of the applicator tip described above. Simultaneously, in step 1420, the light assembly 100 performs a process of emitting pulses of light to the skin surface are of the user according to the light emission of the specific light described above. These two processes can be started and ended at separate times according to separate on/off switches, or they can be started and ended simultaneously according to the same on/off switch (such as the on/off switch shown in FIG. 8).

Numerous modifications and variations of the present disclosure are possible in light of the above teachings. It is therefore to be understood that within the scope of the appended claims, the claimed invention may be practiced otherwise than as specifically described herein.

What is claimed is:

1. An apparatus comprising:
an applicator assembly that includes a motor configured to drive an applicator tip in a predetermined motion to apply a cyclical mechanical force to a skin surface area of a user and the applicator assembly being configured to deliver a skin formulation to a skin surface area of the user, the predetermined motion having an amplitude of motion substantially perpendicular and parallel to a surface of a skin region such that an amount of surface area of the applicator tip in contact with the skin increases along with an amount of movement of the applicator tip in a parallel direction to the skin surface during each cycle of motion of the applicator tip; and
an electromagnetic energy assembly that includes a plurality of electromagnetic energy sources, which surround the applicator assembly such that the plurality of electromagnetic energy sources are disposed along a perimeter of a region that includes the applicator assembly, and which are configured to deliver pulses of electromagnetic energy stimulus of a character and for a duration sufficient to penetrate one or more dermal layers within the skin surface area of the user,
wherein the skin formulation delivered to the skin surface area by the applicator tip is configured to interact with the pulsed electromagnetic energy stimulus, and,
wherein at least one electromagnetic energy source is fixed adjacent and external to an outer edge of the applicator assembly, the plurality of electromagnetic energy sources being fixed without undergoing the predetermined motion of the applicator tip.

2. The apparatus according to claim 1, wherein the plurality of electromagnetic energy sources each comprise a plurality of light-emitting diodes and is configured to concurrently or sequentially generate at least a first continuous electromagnetic energy stimulus having a peak emissive wavelength of about 590 nanometers and a second continuous electromagnetic energy stimulus having a peak emissive wavelength ranging from about 850 nanometers to about 870 nanometers.

3. The apparatus according to claim 1, wherein the plurality of electromagnetic energy sources are each configured to produce a single dominant emissive wavelength via narrowband multichromatic radiation.

4. The apparatus according to claim 3, wherein the single dominant emissive wavelength is about 590 nanometers.

5. The apparatus according to claim 1, wherein the plurality of electromagnetic energy sources each include at least one light emitting diode (LED).

6. The apparatus according to claim 5, wherein the at least one light emitting diode (LED) includes a first LED which emits light at a dominant emissive wavelength of about 590 nanometers and a second LED which emits light at about 850-870 nanometers.

7. The apparatus according to claim 6, wherein the first light emitting diode (LED) emits visible yellow light and the second LED emits infrared light.

8. The apparatus according to claim 7, wherein a ratio of power radiation of the first light emitting diode (LED) to the second LED is about 4:1.

9. The apparatus according to claim 8, wherein the first light emitting diode (LED) emits light at about 2 milliwatts per square centimeter (mW/cm$^2$) and the second LED emits light at about 0.5 mW/cm$^2$.

10. The apparatus according to claim 1, wherein an energy fluence of the electromagnetic energy assembly received at the skin surface area is less than about 4 J/cm$^2$.

11. The apparatus according to claim 1, the electromagnetic energy assembly further comprising a diffusing lens configured to diffuse light emitted from the electromagnetic energy assembly on the skin to spread an interrogation region.

12. The apparatus according to claim 1, wherein the plurality of electromagnetic energy sources each emit pulses of light to the skin surface area of the user at a frequency of about 3 Hz.

* * * * *